United States Patent [19]
Ratzenberger et al.

[11] Patent Number: 5,753,273
[45] Date of Patent: May 19, 1998

[54] SYSTEM FOR MONITORING AND CONTROLLING THE MATERIAL COMPOSITION AND PLASTIC OR DUCTILE DEFORMATION OF THE MASS FLOW IN A MACHINE

[75] Inventors: Hansgeorg Ratzenberger, Weimar; Volker Gröber, Jena, both of Germany

[73] Assignee: innovatheim Prof. Dr. Leisenberg GmbH & Co. KG, Butzbach, Germany

[21] Appl. No.: 702,650

[22] PCT Filed: Dec. 23, 1995

[86] PCT No.: PCT/DE95/01866

§ 371 Date: Aug. 28, 1996

§ 102(e) Date: Aug. 28, 1996

[87] PCT Pub. No.: WO96/20396

PCT Pub. Date: Jul. 4, 1996

[30] Foreign Application Priority Data

Dec. 28, 1994 [DE] Germany .................... 44 46 933.0

[51] Int. Cl.⁶ .................................................. B29C 47/92
[52] U.S. Cl. ................. 425/131.1; 425/135; 425/145; 264/40.1; 264/40.7
[58] Field of Search .................. 264/40.7, 40.1; 425/131.1, 140, 143, 144, 145; 73/87, 104

[56] References Cited

U.S. PATENT DOCUMENTS

| 4,097,566 | 6/1978 | Bertin et al. . | |
|---|---|---|---|
| 4,609,336 | 9/1986 | Stevenson et al. . | |
| 5,225,209 | 7/1993 | Hayashi | 425/145 |
| 5,520,870 | 5/1996 | Allan et al. | 425/145 |

FOREIGN PATENT DOCUMENTS 3434904 10/1985 Germany .
3915279 11/1990 Germany .
4113746 4/1992 Germany .
4446933 3/1996 Germany .

OTHER PUBLICATIONS

Automatic Penetrometer AP 4/2.

Fortschrittsberichte . . . Gesellschaft; 2/3 Jun. 1992.

Siegfried Bostrom; Kautschuk–Handbuch; 29 Aug. 1972; pp. 130–139.

*Primary Examiner*—Khanh P. Nguyen
*Attorney, Agent, or Firm*—Robert W. Becker & Associates

[57] ABSTRACT

A system for monitoring and controlling the composition and the plastic deformation of material being processed in a processing machine has at least one measuring arrangement that includes a first pivotable lever connected to the processing machine at a location where the material flows. The first pivotable lever is biased by a force such that the first pivotable lever contacts the material with a force component acting at a right angle onto the surface of the material. A penetration body is connected to the first pivotable lever at an end thereof facing the material. The penetration body has a wedge shape tapered in a direction toward the surface of the material. A first travel sensor for sensing the depth of penetration of the penetration body into the material is provided. The first travel sensor is fixedly connected to the processing machine and cooperates with the first pivotable level at a distance from the penetration body. A second travel sensor for sensing the advancing speed of the material is substantially stationarily connected to the processing machine in the advancing direction of the material. A processing unit for processing signals received from the first and second travel sensors is provided. A control member for controlling the composition of the material is connected to the processing unit.

14 Claims, 8 Drawing Sheets

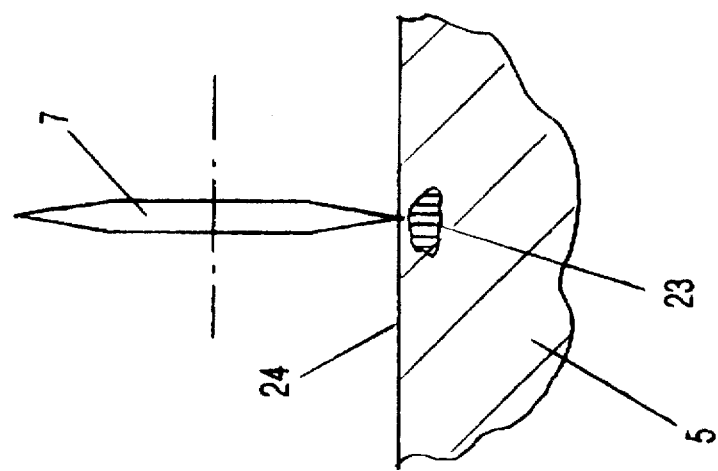
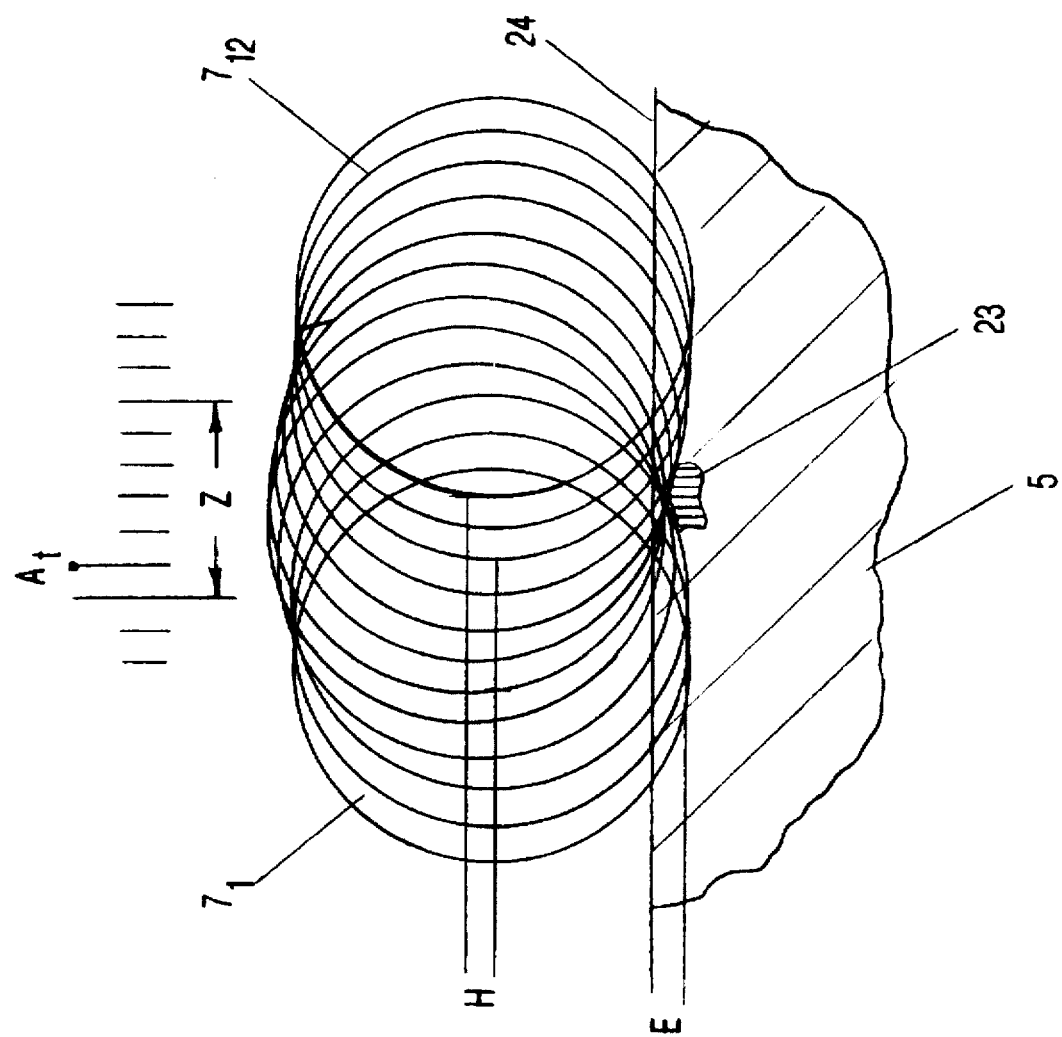
FIG-7

SYSTEM FOR MONITORING AND CONTROLLING THE MATERIAL COMPOSITION AND PLASTIC OR DUCTILE DEFORMATION OF THE MASS FLOW IN A MACHINE

BACKGROUND OF THE INVENTION

The invention relates to a system for monitoring and controlling the material composition and plastic or ductile deformation of the mass flow of a machine.

The invention is to be used where a mass flow that is plastically deformable, respectively, that in a ductile state can be deformed or is deformed, occurs in a production process. This relates especially to processes in the ceramics industry and the manufacture of food stuffs.

Known are measuring devices for determining the material consistency, which are called penetrometer. The penetration body can be in the form of a needle, a rod, a cone, a ball or similar shapes. Its size can be between that of a match and that of a pencil. The penetration occurs under free fall conditions for predetermined loading or supported by spring force. The penetration depth into the material to be examined is measured. When needed, it is also possible for a suitable penetration body to measure the time-dependent course until the end of penetration is reached. The depth of penetration is used as a parameter for the material consistency. (Manual to "Automatisches Penetrometer AP 1" Hersteller: VEB Feinmeß Dresden, 1972) and (U. Hoffmann und D. Mannheim: "Anwendung des Federpenetrometers' Solitest" in "Die Ermiftlung von praxisorientierten Kenndaten zur Charakterisierung von Tonen und tonkeramischen Massen", Fortschrittsberichte der DKG, Vol. 8 (1993) issue 1—Charakterisierung toniger Rohstoffe und tonkeramischer Massen—).

The Penetrometer allows measurements only to be carried out by hand or to be initiated by hand, which measurements are performed at discrete intervals.

In Boström, S.: Kautschuk-Handbuch, Berliner Union Stuttgart 1962 p. 131–138, the different devices for measuring softness and hardness are disclosed. A softness testing is very similar to the hardness testing according to Brinell and differs only in that the ball diameter is greater (10 mm instead of 5 mm) and the load is less (1000 g instead of 50 kg). The softness test numbers result as the difference between the penetration depth of a polished hardened steel ball with a preload of 50 g and a main load of 1000 g.

From German Patent 34 34 904 a method and a device for monitoring a continuously extruded profiled band comprised of one or a plurality of mixtures or a thermoplastic material. The length shrinkage values of the profiled band resulting along a cooling path are determined mechanically/electrically or optically/electronically and the sensed values are sent to a control device connected to a scale, measuring the meter weight, which control device thus adjusts the nominal shrinkage values.

In U.S. Pat. No. 4,097,566 and U.S. Pat. No. 4,609,336 solutions are disclosed which, also based on electronic and/or mechanical measuring sensors, determine the dimensions of an extruded foil band and the control parameters for affecting the dimensions of the foil band.

With the disclosed devices a continuous measurement of the consistency or softness or hardness is not possible. With the disclosed measuring methods it is impossible to deduce the material composition of a mixture.

The invention has the object of solving the problem of continuously analyzing mass flows in production processes in order to determine, based on the measured values, characteristic parameters of the production process and of the material composition and to save those values which serve for the material analysis and/or machine monitoring. The parameters should also serve to determine control parameters for affecting the production process and to document quality assurance of the production process.

SUMMARY OF THE INVENTION

The system for monitoring and controlling the composition and the plastic deformation of material being processed in a processing machine according to the present invention comprises at least one measuring arrangement comprising:

a first pivotable lever connected to the processing machine at a location where the material flows;

the first pivotable lever biased by a force such that the first pivotable lever contacts the material with a force component acting at a right angle onto a surface of the material;

a penetration body connected to the first pivotable lever at an end thereof facing the material;

the penetration body having a wedge shape tapered in a direction toward the surface of the material;

a first travel sensor for sensing the depth of penetration of the penetration body into the material;

the first travel sensor fixedly connected to the processing machine and cooperating with the first pivotable level at a distance from the penetration body;

a second travel sensor for sensing the advancing speed of the material;

the second travel sensor substantially stationarily connected to the processing machine in the advancing direction of the material;

a processing unit for processing signals received from the first and second travel sensors;

a control member for controlling the composition of the material, the control member connected to the processing unit.

The processing machine preferably comprises a press with a die and the first pivotable lever is connected downstream of the die.

Expediently, weights are connected to the first pivotable lever for generating the force.

The penetration body is a wheel rotatably supported at the first pivotable lever, the wheel tapering in a wedge shape radially outwardly so as to form a cutting edge, wherein the cutting edge has a radius of 0.01 mm to 2 mm and wherein the wheel has an outer diameter of 1 cm to 10 cm.

A deflection of the penetration body about a pivot axis of the first pivotable lever is sensed by the first travel sensor and wherein the second travel sensor includes a wheel and a rotational angle transmitter connected to the wheel.

The penetration body is a stationary gliding body being conically shaped so as to taper in a direction toward the surface of the material, the gliding body having a cutting edge of a radius of 0.01 mm to 2 mm, the system further comprising a second pivotable lever, the second travel sensor connected to the second pivotable lever and including a wheel contacting the surface of the material and a rotational angle transmitter connected to the wheel.

The system preferably further includes means for measuring chemical and physical properties. The means include means for measuring electrical conductivity and/or means for measuring the temperature of the material.

In another embodiment of the present invention, a partial mass flow is branched off the material, measurements are performed on the partial mass flow, the partial mass flow is returned, and subsequently the composition of the material is adjusted by the control member.

The system may further comprise a linear guide to which the second lever with the wheel is connected, the linear guide positioned at a selectable slant to the vertical. An angle member may be provided to which the first pivotable lever is pivotable connected. The angle member is displaceable relative to the second pivotable lever and by displacing the angle member an angle between the first pivotable lever and the surface of the material is selectable. The arrangement of the first and the second levers and the respective length of the first and the second pivotable levers are selected such that an axis of rotation of the wheel is positioned vertically above a point of contact of the penetration body at the surface of the material.

The penetration body and the wheel are supplied with an electrical voltage for cleaning purposes.

The processing machine comprises a press, wherein the penetration body, the wheel, and the press are electrically insulated from one another so that between the penetration body, the wheel, and the press electrical conductivity measurements are performed.

The system may further comprise two of the at least one measuring arrangements, wherein a first one of the measuring arrangements is positioned upstream of the processing machine and a second one of the measuring arrangements is positioned downstream of the processing machine.

The system for monitoring and controlling the material composition and the plastic or ductile deformation of the mass flow is arranged at a machine which shapes a branched-off part of the mass flow to a profiled mass strand only for the purpose of measuring or which produces from the entire mass flow a profiled mass strand as an intermediate product to be measured. The system is comprised of a lever pivotably supported at the machine which is loaded by a force. One force component acts at a right angle to the direction of movement of the profiled mass strand or the shaped body. At the lever, at the end facing in the direction of the profiled mass strand or the shaped body, a penetration body is arranged which in the direction toward the profiled mass strand or shaped body tapers wedge-shaped. A first travel sensor for determining the depth of penetration of the penetration body into the profiled mass strand or shaped body cooperates at a distance from the penetration body with the lever and is stationary with respect to the machine.

A second travel sensor for determining the advancing speed of the profiled mass flow is stationarily arranged at the machine and is in contact with the profiled mass strand. This portion of the system provides a continuously operating penetrometer.

In a further part of the system the signals which are detected by deflection of the first travel sensor and the signals resulting from the second travel sensor are guided into an evaluation, logging, memory and/or control unit (processing unit) which is connected to at least one control member.

The evaluation, logging, memory, and/or control unit serves as a production monitoring and production control device.

The term "machine for plastic or ductile processing and deformation of a mass flow" according to the present invention includes devices which are used in industrial areas for material transformation and material shaping, especially in the food stuffs industry, the chemical industry, the ceramics industry, and the construction industry. They are used where plastic or ductile materials are manufactured as starting materials, intermediate products, or end products, i.e., where machines mix components, adjust the plasticity and ductility, prepare homogenous mixtures and form (press) profiled mass flows or shaped bodies.

The system can be arranged at the inlet of the machine, at the outlet of the machine, or within the machine along the course of the machining process.

In a first embodiment, the penetration body is a running wheel rotatably connected to a lever end which wheel in the direction of the radially outer diameter is wedge-shaped whereby the wheel edge has a radius of 0.05 mm to 2 mm. The deflection of the wheel about the lever axis is logged with the first travel sensor and the velocity of the mass strand is logged with the second travel sensor which is embodied as a rotational angle transmitter and cooperates with the wheel.

In a second embodiment the penetration body is a stationary gliding body which has a conical shape and an edge of a radius of 0.05 mm to 2 mm. For measuring the velocity of the profiled mass strand, the second travel sensor is provided which is embodied as a running wheel connected to a further lever and contacting the profiled mass strand whereby the running wheel cooperates with a rotational angle transmitter.

With the aid of the system the simultaneous detection of further chemical and/or physical characteristic values is enabled, for example, the electrical conductivity of the mass strand, the material temperature, and the electrical power output of the corresponding drive units, in order to continuously detect characteristic parameters of the production process.

The evaluation, logging, memory and/or control unit is connected to at least one control member of the machine with which at least one component of the composition of the mass flow to be processed within the processing machine is adjustable. Control members can be arranged at the inlet of the machine as well as at the outlet of the machine.

The measurement can be performed, for example, on the formed profiled mass strand (intermediate product) or on a partial mass flow branched off from the manufacturing process and profiled to a measuring mass strand at which measurements are to be performed. The material of the measuring mass strand is returned to the main flow after measurement.

The adjustment/correction of the mass is possible before or after separation of the mass flow with the aid of a control member, for example, for moisture adjustment.

Identical measuring devices can be positioned upstream of the processing machine (for example, a strand press) for monitoring the composition of the green product (mass flow) and downstream of the processing machine for monitoring the processing machine and the intermediate or end products (mass strand or shaped product). The resulting measured values are fed into the evaluation, logging, memory and/or control unit.

With the aid of the invention it is possible to continuously monitor evaluate, directly actively influence, and document the production process.

The measured values produced with the aid of the measuring system contain short term and long term information.

The short term information provides information in regard to a momentary proportion of coarse particles and the momentary moisture contents of the material (as a parameter for the ductility).

The long term information serves to control, monitor as well as document the production. Averaging in certain time intervals provides a means for determining the consistency of the mass flow (for example, moisture contents).

The values of average amplitude within the time interval and/or the period length provide information on the profiled member or the press.

BRIEF DESCRIPTION OF THE DRAWINGS

The invention will be disclosed with the aid of an example of a process in the ceramics industry. It is shown in:

FIG. 7 a schematic representation of sensing of a coarse particle in a profiled mass strand;

DESCRIPTION OF PREFERRED EMBODIMENTS

Figure 1:
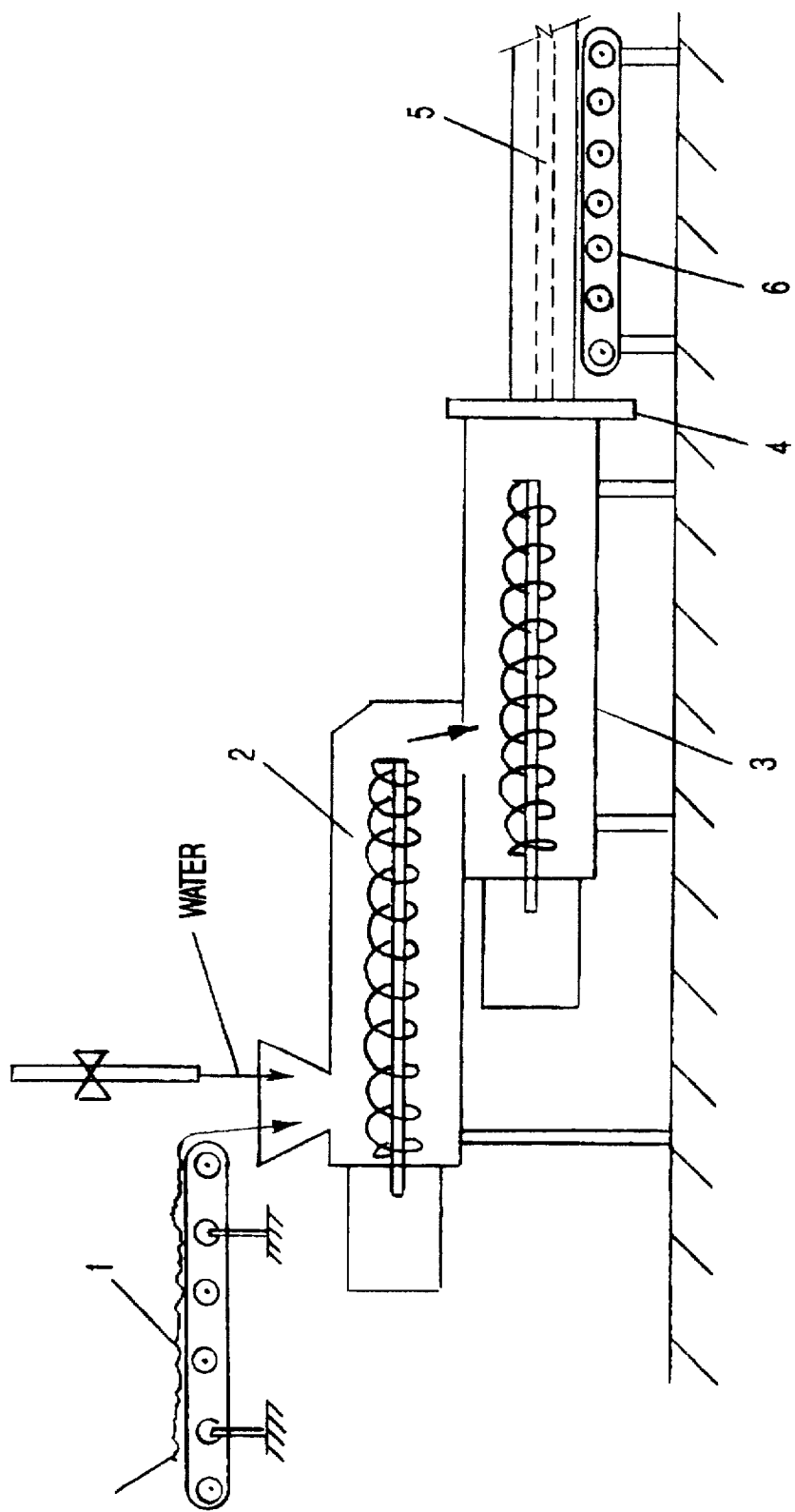
FIG. 1 the last processing step for manufacturing an extruder pressed profiled mass strand.

According to FIG. 1 a mass flow 1 (for example, clay) being processed is introduced into a preparation device 2 in which water is added to the mass flow, if needed, and in which the mass flow is intensively mixed. The processing device 2 conveys the mass flow into a press 3 whereby with the aid of a die 4 a profiled mass strand 5 is generated. The profiled mass strand 5 is supported by a transporting belt 6, is conveyed farther and subjected to further processing.

The system serves for monitoring the momentary consistency and composition, especially of the coarse particle contents and the processing moisture of the mass flow 1 being processed, respectively, of the mass strand 5 and/or of the process of producing the mass strand 5.

Figure 2:
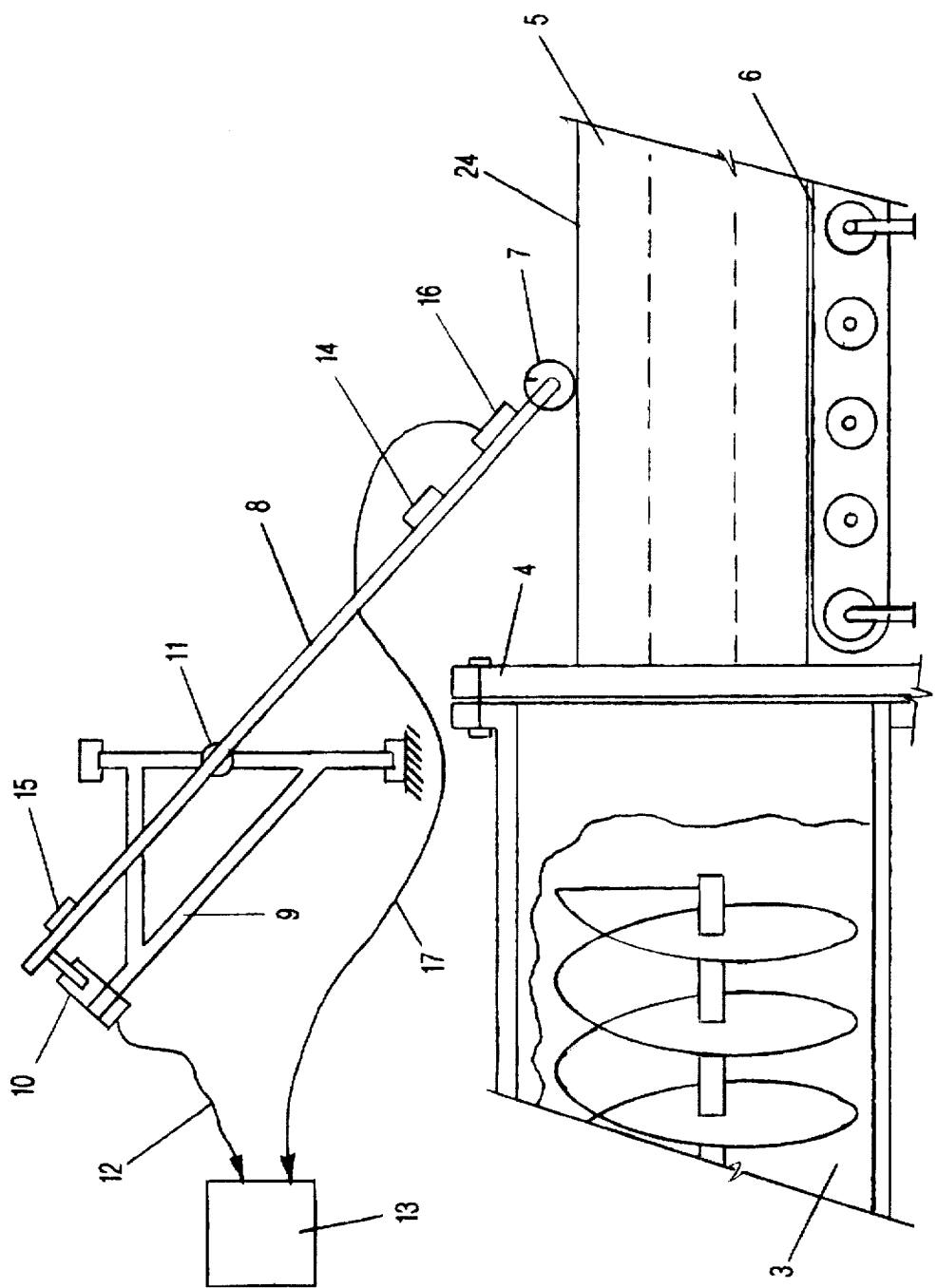
FIG. 2 a continuously registering penetrometer with integrated device for simultaneous detection of the advancing speed of the mass strand.

The part of the system, which is named a continuously measuring penetrometer, is comprised, according to FIG. 2, of an easily rotatable penetration body 7 which rolls along the mass strand 5 and, in the shown example, is a running wheel that is connected to a play-free supported lever 8.

The support action of the lever is provided by a holder system 9 at an angle of approximately 45° to the surface 24 of the mass strand 5. The holder system 9 is stationarily arranged relative to the die 4.

The lever 8 has coordinated therewith at a distance to the penetration body 7 a travel sensor 10. Depending on the type of travel sensor 10 and the properties of the mass strand 5 to be measured a certain lever transmission can be selected.

In the shown embodiment, the travel sensor is positioned above the pivot point 11 of the lever 8. The travel sensor 10 is connected with a measuring line 12 to a suitable measuring and evaluation system 13.

The adjustment of the penetration pressure force of the penetration body 7 into the mass flow 5 is performed by mounting load weights 14 and/or counter weights 15 and is adjusted to a constant value. In this context, the oscillation and inertia behavior of the system penetration body/lever/ penetration pressure force/measuring sensor on the measuring detection must be taken into consideration.

As a function of the consistency of the mass strand 5 and its compensation the penetration body penetrates to a different depth into the mass strand. A change of penetration depth is registered over time. As a function of the velocity of the mass strand 5 the rotating penetration body (running wheel) is moved at different velocities. Since, in practice, fluctuations of the advancing speed of the mass strand will occur, it is necessary to take into consideration the advancing speed of the mass strand into the data acquisition process. For this reason, a travel sensor 16 is coordinated with a penetration body 7 which is in the form of a running wheel. The travel sensor 16 is mounted at the lever 8 in the vicinity of the bearing of the running wheel and detects the rotational movement of the running wheel. For data acquisition the travel sensor 16 is connected with a measuring line 17 to the measuring and evaluation device 13. When the penetration body 7 is embodied as a running wheel, its diameter is approximately 5 cm. The cutting edge penetrating into the material is rounded so as to have a radius of 0.1 mm. The embodiment of the cutting edge has an effect on the measuring behavior. A penetration body with a pointed cone or sharp gliding or running surface reacts when under a reduced load more sensible to differences in grain structure than a penetration body with greatly rounded portions at increased loads or inertia.

Depending on the composition of the clay raw material, respectively, of the mass flow 1 and in first approximation, depending on the momentary contents of moisture of the mass strand 5, the penetration body 7 is impressed deeper or less deep into the mass strand 5. The penetration body 7 reacts, however, not only with regard to the momentary consistency of the mass strand 5, but also with respect to coarse particles contained within the mass, to shaping influences and other effects.

The continuously slightly changing penetration movement is detected by the travel sensor 10. The measured values of the travel sensor 10 and the measured values of the travel sensor 16 are saved with the aid of special hardware and software in a computer of the measuring and evaluation device, are graphically represented, and mathematically-statistically processed.

Figure 3:
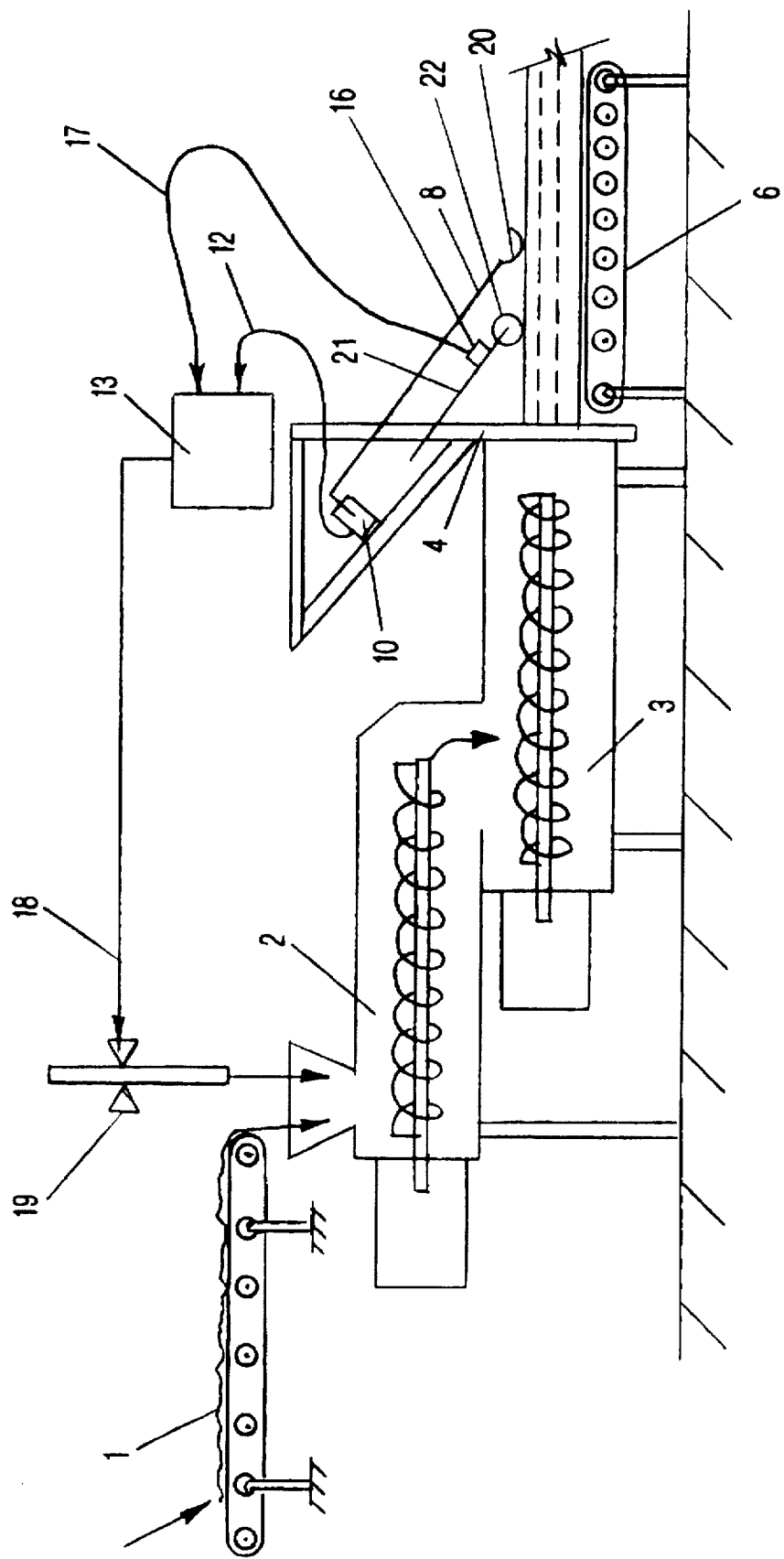
FIG. 3 an arrangement for monitoring and controlling a machine for plastic deformation of a mass flow.

FIG. 3 shows an arrangement for monitoring and controlling a machine for plastic deformation of a mass flow. Upon reaching limits, which are determined by the evaluation, logging, memory and/or control unit 13, control values, for example, for water metering are provided to the metering system 19 via control lines 18.

In FIG. 3 the continuously measuring penetrometer is modified with respect to the one of FIG. 2. Accordingly, the penetration body 7 can also be embodied as a gliding body 20. In this embodiment, the measurement of the advancing speed is expediently performed with a separate system. For this purpose, a second lever 21 with a second running wheel 22 is arranged together with the travel sensor 16 such that a continuous uniform contact with the surface 24 of the mass strand 5 is ensured.

With the aid of the second running wheel 22 it is advantageous to perform further measurements of physical and chemical parameters, as, for example, measuring of the electrical conductivity.

With the aid of the invention it is possible to constantly monitor, evaluate, directly actively influence, and document the production process.

The measured values, which are acquired by the continuously sensing penetrometer, contain short term and long term information.

Figure 4:
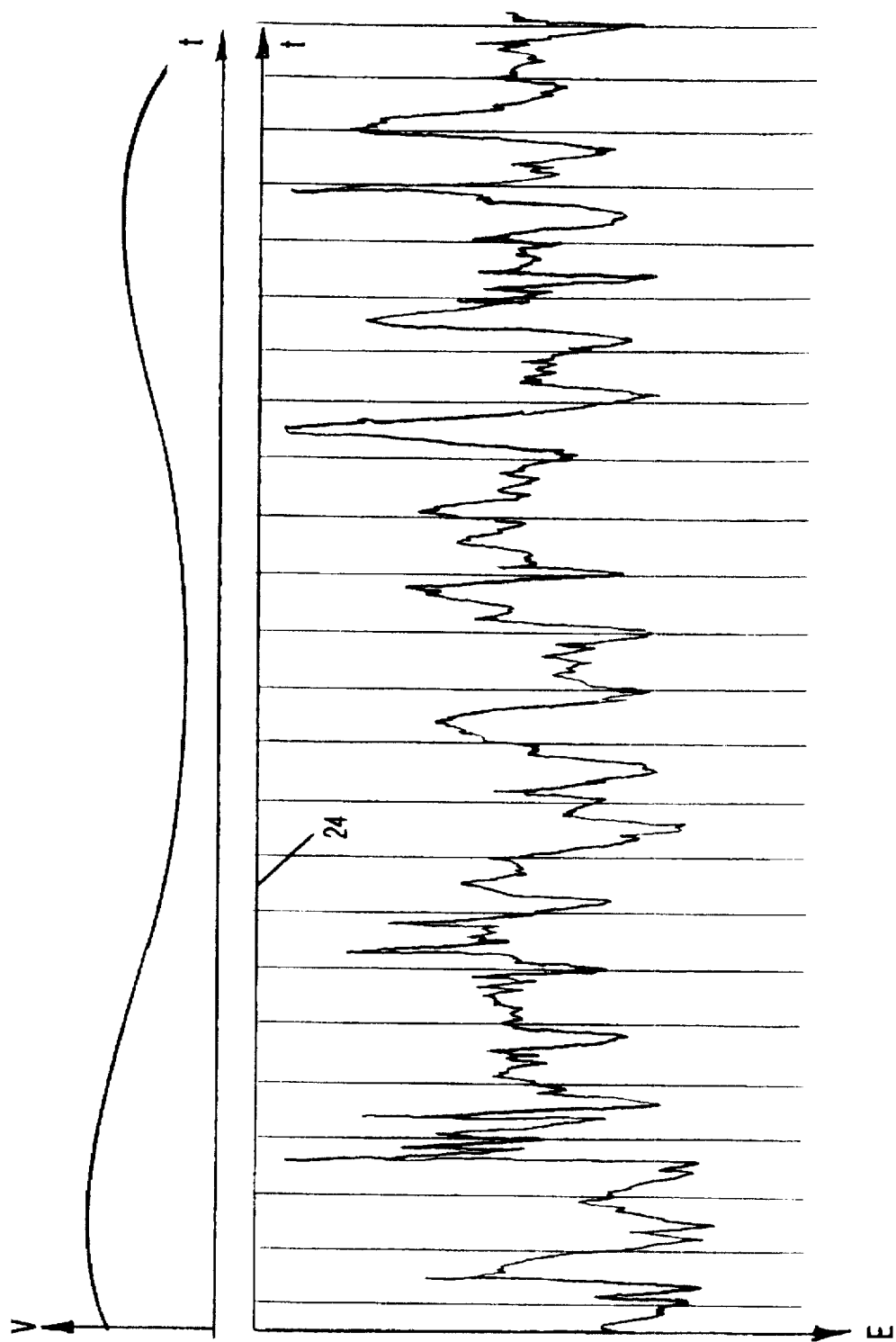
FIG. 4 a representation of measured values as a function of time.

FIG. 4 shows an example of a graphically represented short term information over a measuring period of approximately 1 minute acquired at an actual mass strand. The upper curve represents the change of the velocity of the mass strand 5 as a function of time. The lower curve shows the change of penetration depth E of the penetration body 7 into the mass strand 5 as a function of time.

Figure 5:
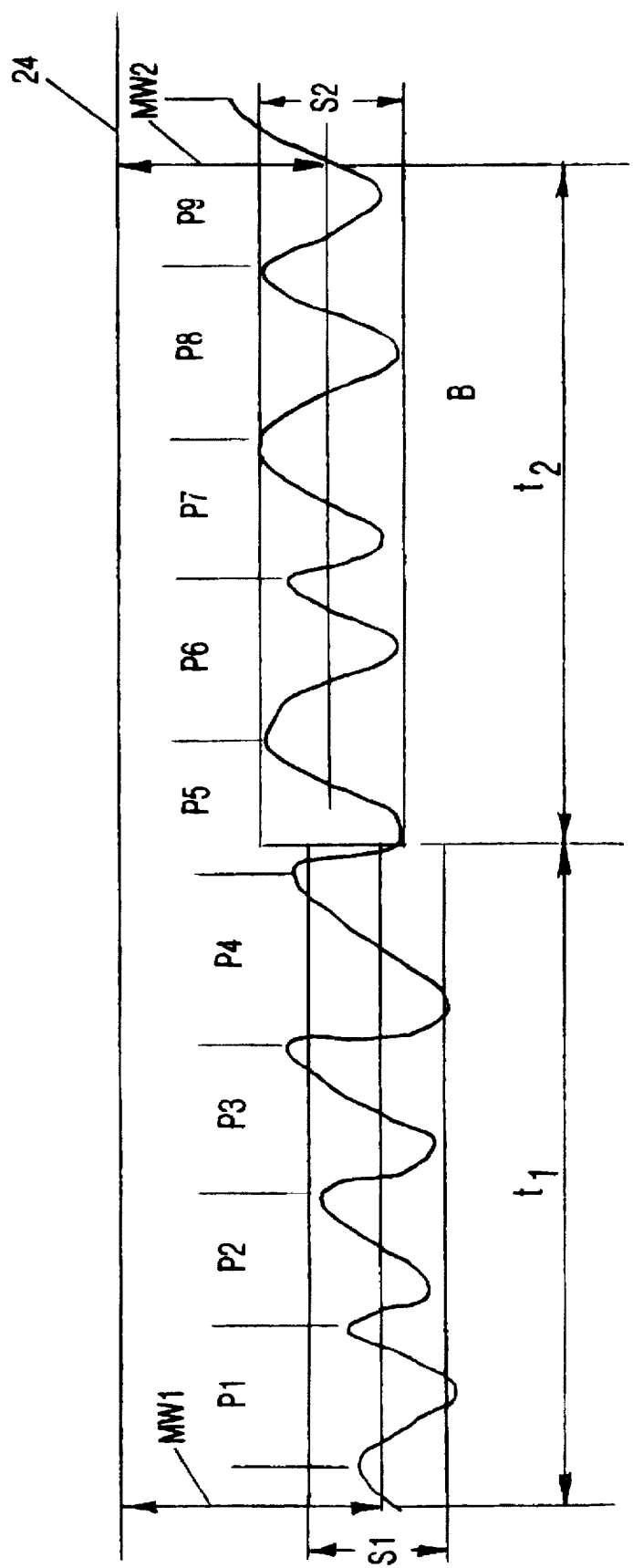
FIG. 5 a schematic illustration for sensing measured values.

FIG. 5 is a schematic representation of the base line B of the information contained within the measured data. Under the premise of a constant material composition, an average value $MW_1$ of the penetration depth over a period t1 of, for example, one minute a value for the momentary consistency, respectively, the momentary moisture contents is provided.

The average value $MW_1$ corresponds to the nominal value. For a minimal moisture contents of the mass a reduced average penetration depth results in the following measuring period t2 which results in an average value $MW_2$.

These fluctuations are used, depending on intensity and respective frequency of the time intervals, for activating the control members for metering the amount of moisture. The number of measuring periods should be as great as possible.

The periods $P_1$ to $P_9$ etc. are specific machine parameters and they are evaluated for monitoring the operation of the press 3 and the conveyor belt 6. The same holds true for the average amplitude heights $S_1$ and $S_2$ etc. in the respective time interval (range of fluctuation).

Figure 6:
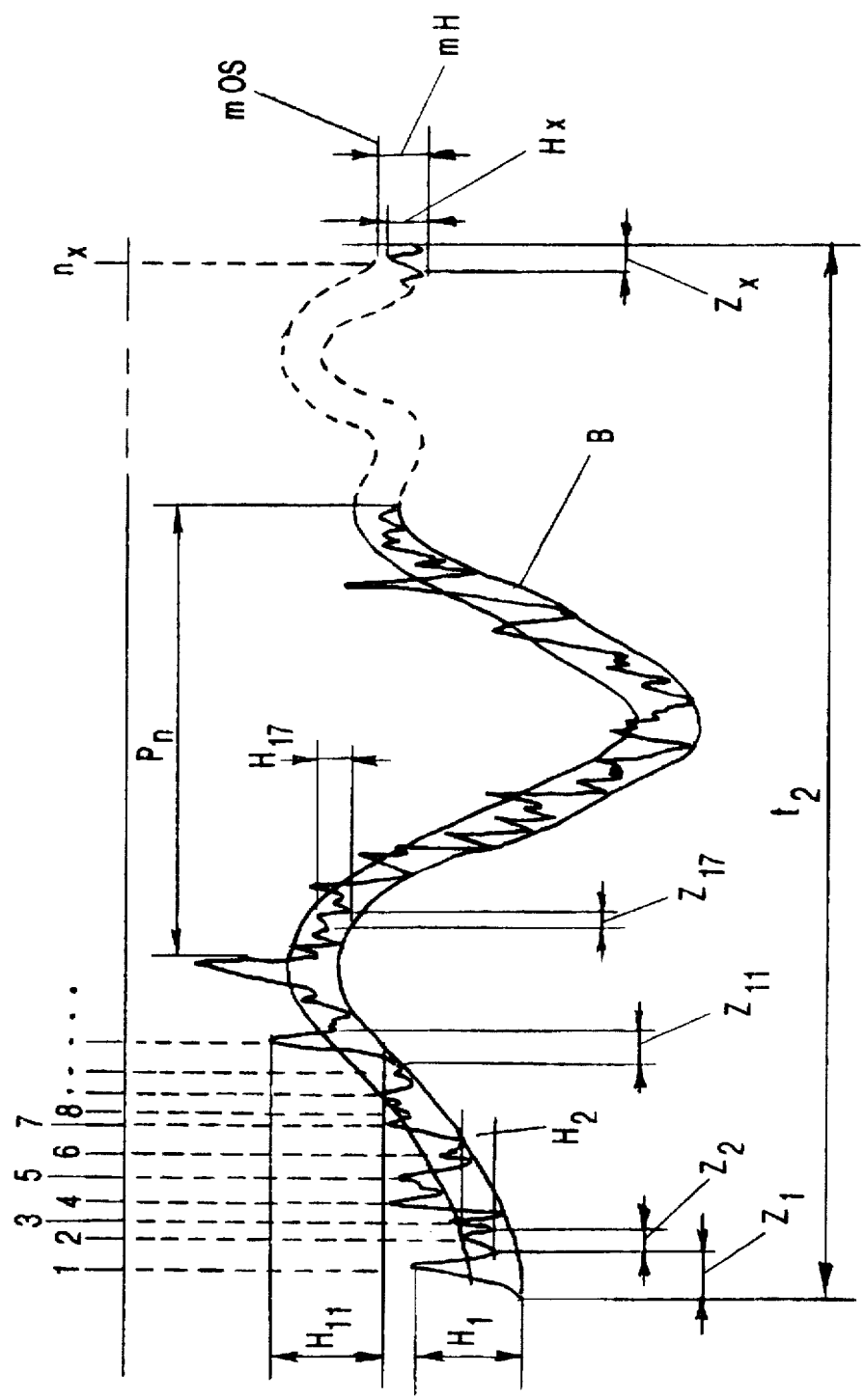
FIG. 6 an enlarged representation of the measured values.

The zoomed curve portion represented in FIG. 6 shows that the base line B of the measuring curve has "high frequency" oscillations in the form of artifacts or transients overlapping them. These oscillations have their cause in the coarse grain contents of the mass.

Their frequency is within a range of magnitude between approximately 0.1 and 10 hertz. The parameter MH is the average amplitude height of the harmonic oscillations, the parameter H is the height of the individual harmonic oscillations resulting from the particle size, the parameter Z is the base width of the individual harmonic oscillations resulting from the coarse grains, and the parameter N is the number of harmonic oscillations per time unit.

FIG. 7 shows how a coarse particle 23 in the surface 24 of the mass flow impedes the penetration of the penetration body 7. The positions $7_1$ to $7_{12}$ of the penetration body 7 illustrate in which manner in the example of FIG. 6 an amplitude height H and a base width Z result. At in this context means the sensing time (sensing rate) in which in an electronic manner the change of penetration depth E is sensed.

The number of these harmonic oscillations $n_x$ per time unit is a measure for the amount of coarse particles to be detected within this time period; their average range of fluctuation and the average amplitude height mH are a measure for the detected average particle size. The intensity of each individual harmonic oscillation, i.e., the amplitude height H of each individual oscillation ($H_1$, $H_2$, $H_3$ etc.) and the base width Z of each individual oscillation ($Z_1$, $Z_2$, $Z_3$ etc.) is a measure for the size of each individually detectable particle.

Thus, based on the frequency and intensity of the harmonic oscillations, determinations with respect to the coarse particle proportions within the clay strand can be derived. With the aid of special statistic computer processing program, the momentary coarse grain proportion and its grain distribution are determined over the respective measuring time period.

For a constant material use it is thus possible to provide a monitoring of the processing intensity of the respective processing device. When, for constant technological conditions, the consistency of the mass (for example, based on fluctuations in the mineralogical and granular size composition of the basic materials) changes, these fluctuations are also detected and can thus be used, for example, for automatic corrections of metering of the individual materials and/or of the moisture contents for pressing, while also taking into consideration the electrical power use of the drive units.

The long term information of the measured values is based on the detection and memorization of the averaged values of the short term measurements within the individual measuring intervals. Thus, with respect to ISO 9,000 etc., the possibility for representing, memorizing and documenting processes, for example, over the period of a workshift or an entire year can be provided for the purpose of long term production control and evaluation.

When, in addition to measuring the penetration depth with the continuously sensing penetrometric sensor and also the advancing speed, the measured values of electrical conductivity and electrical power use of the drive units are sent to the computer, then it is possible, based on the three measured values and with the aid of a statistical processing program, to analyze the moisture contents, coarse particle proportion, fluctuations in the material composition, and the operating protocol of the shaping device.

The reason for the additional use of the electrical conductivity of the material to be tested and of the electrical power use of the drive units in the monitoring process is that for a constant mass composition, constant moisture contents, constant mass temperature, and constant measuring conditions, also a constant electrical conductivity in the material and a constant electric use of the drive device should occur. When the mass composition or its moisture contents changes, use the electrical conductivity and also the electrical power of the drive devices should thus also change. Thus, the electrical conductivity and the electrical power use of the drive units are additional parameters for characterizing and monitoring the mass flows and mass strands.

Figure 8:
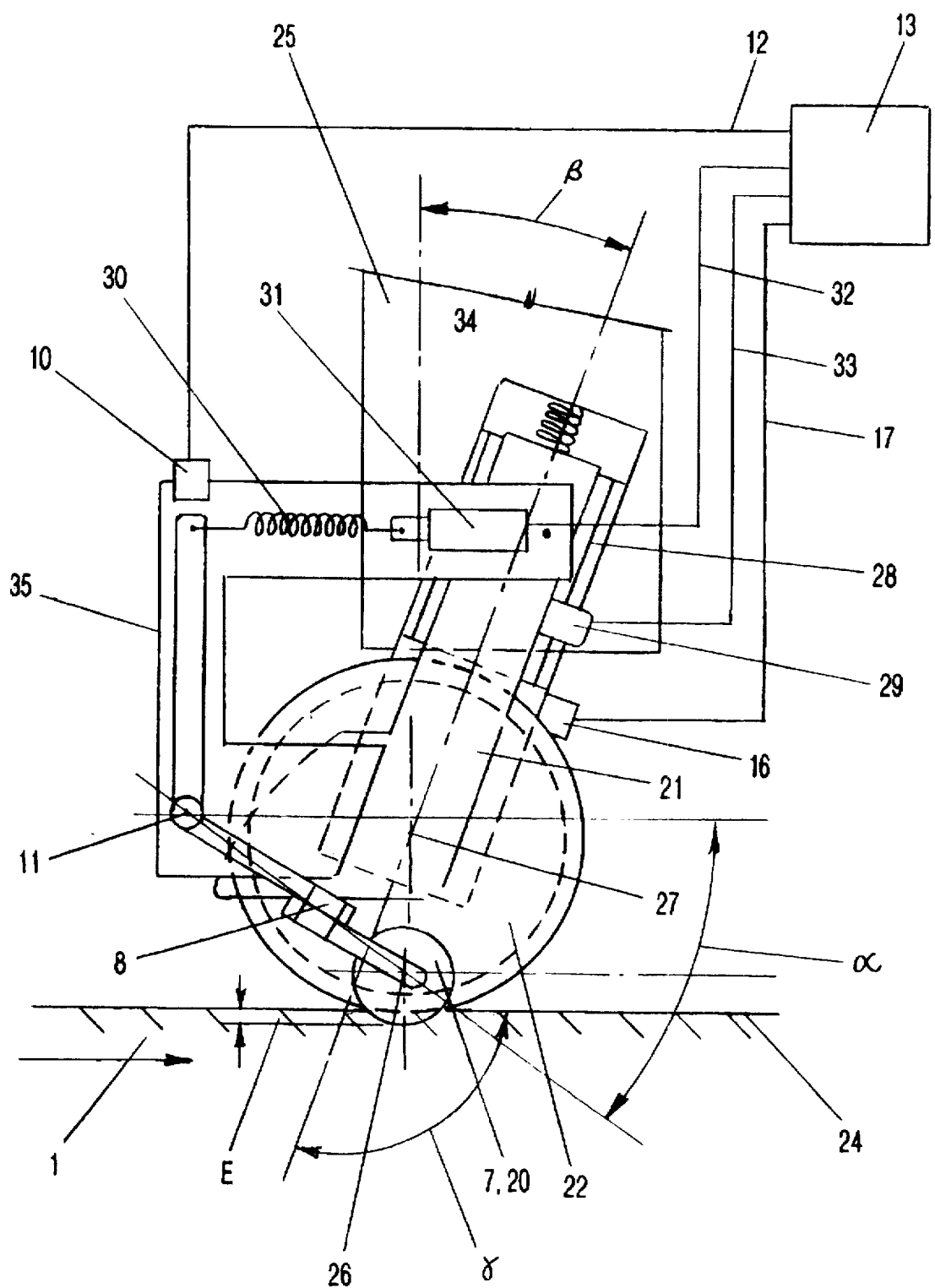
FIG. 8 a continuously registering penetrometer with device for simultaneous detection of the mass strand advancing speed and the macroscopic shape of the strand.

FIG. 8 shows a continuously sensing penetrometer with a lever-supported penetration body 7 in the form of a rotatably supported, conically shaped, tapered sensing wheel.

The sensing wheel, however, can also be exchanged for a non-rotating gliding body (20) or a sensing needle. The sensing wheel is rotatably supported at a first axis of rotation 26 at the end of the lever facing the mass strand. The lever 8 is supported at a first pivot point 11 whereby this pivot location is connected to the second lever 21 with an angle member 35 that is angularly adjustable. The second lever 21 is guided in a linear guide 28 and extends at an adjustable angle β to the vertical toward the surface of the mass strand. The angle β can be approximately 45° relative to the vertical so that the measuring system relative to the direction of the pressed strand is positioned at an angle γ greater/identical to 90°. The pivot point for the adjustment of the angle β is located at the second pivot axis 27.

The first lever 8 is bent at its pivot point by approximately 90° to 140°, and, the first travel sensor 10 is arranged at the end facing away from the mass strand which sensor detects the particle size and consistency of the mass strand.

This part of the lever is connected with a tension spring 30 which is connected with its other end to the second lever 21. The spring 30 has the function of force-loading the penetration body 7 relative to the mass strand. For adjusting the pulling force and thus the pressure force of the penetration body 7, a solenoid 31 is switched between the spring 30 and the second lever 21 which adjusts the prestress of the spring in a stepwise manner. For example, measurements at 80 g or 160 g of weight force can be performed.

The second lever 21 is also angularly designed. The end of the lever facing away from the mass strand is guided in a straight manner in a linear guide 28. The guide 28 is connected to the support 25 which, in turn, is connected to the processing machine. In the area of the bent portion of the second lever 21 a second rotational axis 27 for the second running wheel 22 is provided. The second running wheel 22 detects together with the second travel sensor 16 the advancing speed of the mass strand. A third travel sensor 29 detects the movement transmitted by the second running wheel onto the second lever 21 which results from the macroscopic shape of the mass strand.

The second lever 21 has an adjustment possibility for the angle member 35 which supports the pivot point 11. The pivot point 11 is adjustable with the aid of the adjustment possibility about the first rotational axis 26. Accordingly, the penetration angle α is adjusted whereby the first axis of rotation 26 and the second axis of rotation 27 are approximately (in coarse approximation) perpendicular to the surface of the mass strand.

The distance of the first axis of rotation 26 from the second pivot point 11 is in the range of a few centimeters and is selected such that the approximate vertical line extending through the second axis of rotation 27 and the first axis of rotation 26, viewed in the direction of advancement of the mass strand, is positioned behind the straight line which corresponds to the line of movement of the straight guiding action through the second axis of rotation 27.

Furthermore, between the housing 25 and the second lever 21 a pressure-regulating spring 34 is provided with which it is possible to adjust the contact force of the second running wheel 22 and which furthermore enables the arrangement to be positioned laterally or below (counter to the direction of the weight force).

The first travel sensor 10 is connected via a first measuring line 12, the second travel sensor 16 is connected via a second measuring line 17, the solenoid is connected via a solenoid control line 32, and the third travel sensor is connected via a third measuring line to the evaluation, logging, memory and/or control unit 13.

The penetration body 7 and the running wheel 22 are supplied with an electrical release voltage for cleaning purposes, i.e., by supplying a voltage potential between the body 7 and the wheel 22, on the one hand, and the material to be processed, on the other hand, the material is prevented from adhering to the body 7 and the wheel 22 so that soiling is prevented. Preferably, the penetration body 7 and the second running wheel 22 are electrically insulated from one another. Then it is possible to perform electrical conductivity measurements between the penetration body 7 and/or the second running wheel 22 and/or the press. The present invention is, of course, in no way restricted to the specific disclosure of the specification and drawings, but also encompasses any modifications within the scope of the appended claims.

We claim:

1. A system for monitoring and controlling the composition and the plastic deformation of material being processed in a processing machine, said system comprising at least one measuring arrangement comprising:

a first pivotable lever connected to the processing machine at a location where the material flows;

said first pivotable lever biased by a force such that said first pivotable lever contacts the material with a force component acting at a right angle onto a surface of the material;

a penetration body connected to said first pivotable lever at an end thereof facing the material;

said penetration body having a wedge shape tapered in a direction toward the surface of the material;

a first travel sensor for sensing the depth of penetration of said penetration body into the material;

said first travel sensor fixedly connected to the processing machine and cooperating with said first pivotable lever at a distance from said penetration body;

a second travel sensor for sensing the advancing speed of the material;

said second travel sensor substantially stationarily connected to the processing machine in the advancing direction of the material;

a processing unit for processing signals received from said first and second travel sensors;

a control member for controlling the composition of the material, said control member connected to said processing unit.

2. A system according to claim 1, wherein the processing machine comprises a press with a die and wherein said first pivotable lever is connected downstream of said die.

3. A system according to claim 1, further comprising weights connected to said first pivotable lever for generating said force.

4. A system according to claim 1, wherein said penetration body is a wheel rotatably supported at said first pivotable lever, said wheel tapering in a wedge shape radially outwardly so as to form a cutting edge, wherein said cutting edge has a radius of 0.01 mm to 2 mm and wherein said wheel has an outer diameter of 1 cm to 10 cm.

5. A system according to claim 1, wherein a deflection of said penetration body about a pivot axis of said first pivotable lever is sensed by said first travel sensor and wherein said second travel sensor includes a wheel and a rotational angle transmitter connected to said wheel.

6. A system according to claim 1, wherein said penetration body is a stationary gliding body being conically shaped so as to taper in a direction toward the surface of the material, said gliding body having a cutting edge of a radius of 0.01 mm to 2 mm, said system further comprising a second pivotable lever, said second travel sensor connected to said second pivotable lever and including a wheel contacting the surface of the material and a rotational angle transmitter connected to said wheel.

7. A system according to claim 1, further including means for measuring chemical and physical properties.

8. A system according to claim 7, wherein said means include means for measuring electrical conductivity.

9. A system according to claim 7, wherein said means include means for measuring the temperature of the material.

10. A system according to claim 1, wherein:

a partial mass flow is branched off the material, measurements are performed on said partial mass flow, said partial mass flow is returned, and subsequently the composition of the material is adjusted by said control member.

11. A system according to claim 6, further comprising:

a linear guide to which said second lever with said wheel is connected, said linear guide positioned at a selectable slant to the vertical;

an angle member to which said first pivotable lever is pivotable connected;

said angle member displaceable relative to said second pivotable lever;

wherein by displacing said angle member an angle between said first pivotable lever and said surface of the material is selectable;

wherein the arrangement of said first and said second levers and the respective length of said first and said second pivotable levers are selected such that an axis of rotation of said wheel is positioned vertically above a point of contact of said penetration body at said surface of the material.

12. A system according to claim 6, wherein said penetration body and said wheel are supplied with an electrical voltage for cleaning purposes.

13. A system according to claim 6, wherein said processing machine comprises a press, wherein said penetration body, said wheel, and said press are electrically insulated from one another so that between said penetration body, said wheel, and said press electrical conductivity measurements are performed.

14. A system according to claim 1, comprising two of said at least one measuring arrangements, wherein a first one of said measuring arrangements is positioned upstream of the processing machine and a second one of said measuring arrangements is positioned downstream of the processing machine.

* * * * *